United States Patent
Van Der Heide et al.

(10) Patent No.: US 7,732,629 B2
(45) Date of Patent: Jun. 8, 2010

(54) PROCESS FOR THE PREPARATION OF DIARYL CARBONATE

(75) Inventors: Evert Van Der Heide, Amsterdam (NL); Timothy Michael Nisbet, Amsterdam (NL); Garo Garbis Vaporciyan, Houston, TX (US); Cornelis Leonardus Maria Vrouwenvelder, Amsterdam (NL)

(73) Assignee: Shell Oil Company, Houston, TX (US)

( * ) Notice: Subject to any disclaimer, the term of this patent is extended or adjusted under 35 U.S.C. 154(b) by 230 days.

(21) Appl. No.: 12/017,303

(22) Filed: Jan. 21, 2008

(65) Prior Publication Data

US 2008/0200712 A1 Aug. 21, 2008

(30) Foreign Application Priority Data

Jan. 23, 2007 (EP) .................... 07100959

(51) Int. Cl.
*C07C 69/96* (2006.01)
(52) U.S. Cl. ...................................... 558/274
(58) Field of Classification Search ................. 558/274
See application file for complete search history.

(56) References Cited

U.S. PATENT DOCUMENTS

| 4,554,110 A | 11/1985 | Mark | 260/463 |
| 5,344,954 A | 9/1994 | Schon et al. | 558/274 |
| 5,426,207 A | 6/1995 | Harrison et al. | 558/274 |
| 5,663,480 A * | 9/1997 | Tsuneki et al. | 558/270 |
| 5,747,609 A | 5/1998 | Komiya et al. | 526/68 |
| 7,288,668 B2 * | 10/2007 | Ryu et al. | 558/274 |

OTHER PUBLICATIONS

W B Kim et al., Ind. Eng. Chem. Res., 2004, 43,1897-1914.

* cited by examiner

*Primary Examiner*—Rei-tsang Shiao

(57) ABSTRACT

The invention relates to a process for the preparation of a diaryl carbonate by transesterification of an aromatic alcohol with a dialkyl carbonate in the presence of a transesterification catalyst during a period of time $[t_a]$, in which the aryl moiety is selected from unsubstituted phenyl and mono-, di- and trisubstituted phenyl groups, in which the alkyl moiety is selected from $C_2$ to $C_4$ linear and branched alkyl groups, in which the catalyst concentration is designated $[c_a]$, expressed as gram catalyst per gram of aromatic alcohol and dialkyl carbonate, in which the period of time $[t_m]$ and catalyst concentration $[c_m]$ are determined to arrive at a pre-set approach to the equilibrium for the transesterification of the aromatic alcohol with dimethyl carbonate to methyl aryl carbonate and methanol, in which the product $[c_a]*t_a$ is at least $1.5*[c_m]*t_m$ under otherwise the same reaction conditions.

14 Claims, 1 Drawing Sheet

PROCESS FOR THE PREPARATION OF DIARYL CARBONATE

Figure 1:
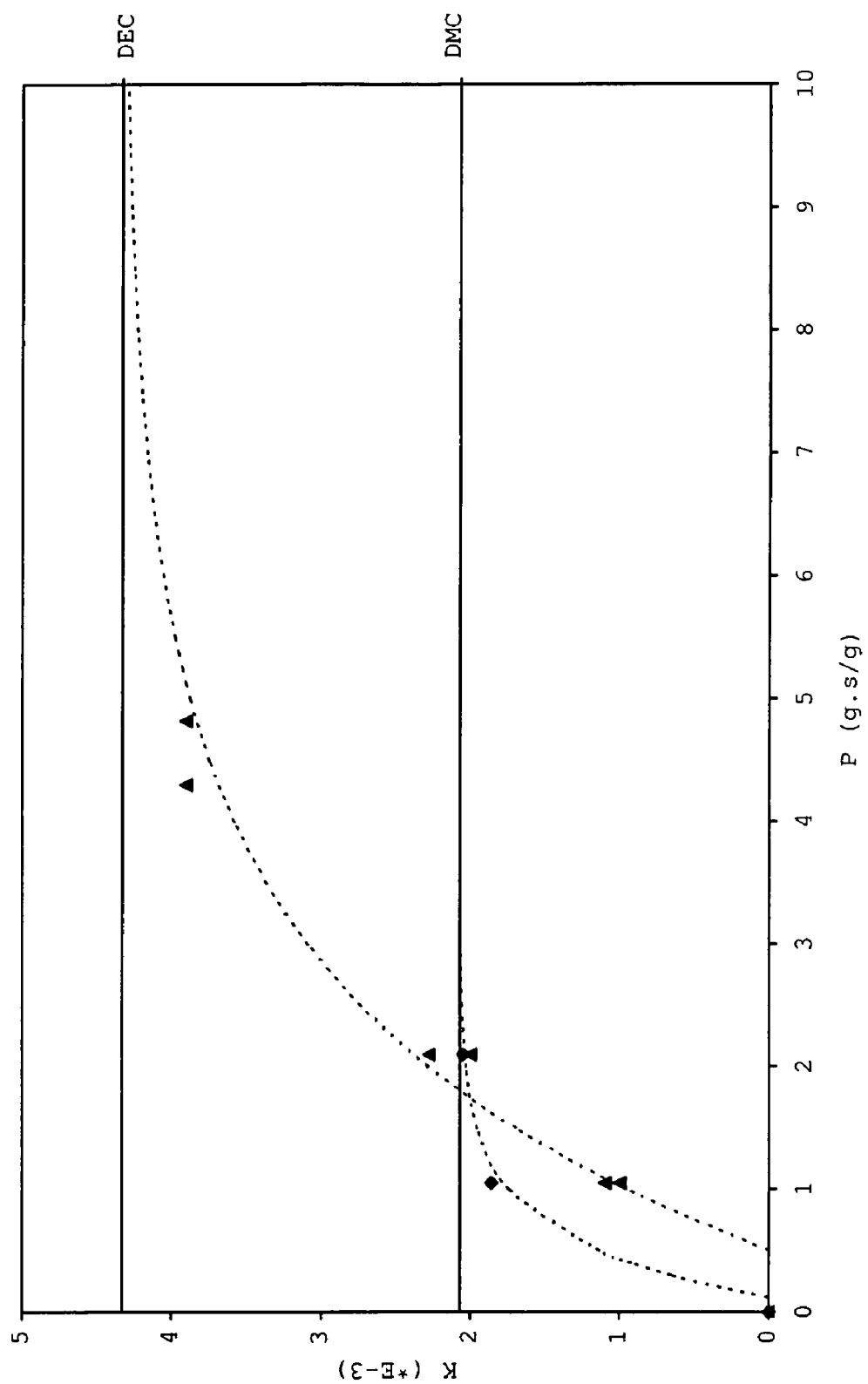

This application claims the benefit of European Patent Application No. 07100959.1 filed on Jan. 23, 2007 that is hereby incorporated by reference.

FIELD OF THE INVENTION

The present invention relates to a process for the preparation of a diaryl carbonate by transesterification of an aromatic alcohol with a dialkyl carbonate in the presence of a transesterification catalyst.

BACKGROUND OF THE INVENTION

A process for the preparation of a diaryl carbonate is described in U.S. Pat. No. 5,344,954. The document discloses a process in which a dialkyl carbonate is converted in two steps. In a first step the transesterification of the dialkyl carbonate with the aromatic alcohol takes place to yield alkyl aryl carbonate and the corresponding alkyl alcohol. The alkyl alcohol is discharged after the first step and the alkyl aryl carbonate is sent to the second step where disproportionation takes place to yield diaryl carbonate that is recovered at the bottom and dialkyl carbonate that is recovered at the top of the reactor in which the second step is conducted. In the second step further transesterification of the alkyl aryl carbonate with any aromatic alcohol that is still present in the reaction mixture also takes place to yield diaryl carbonate and alkyl alcohol. The dialkyl carbonate and the alkyl alcohol that are recovered at the second step are passed to the first step so that the dialkyl carbonate can be reacted again and the alkyl alcohol can be discharged from the first step.

As disclosed in U.S. Pat. No. 5,344,954 it is known that the transesterification reaction of dialkyl carbonate and aromatic alcohol is an equilibrium reaction. The reaction equilibrium limits conversion, even at long residence times. A shift of the equilibrium can be accomplished by removing reaction product. Therefore the steps are conducted as countercurrent transesterification and reactive distillation.

U.S. Pat. No. 5,344,954 discloses a countercurrent transesterification of dialkyl carbonates with aromatic alcohol, in which transesterification the dialkyl carbonates can be dimethyl and diethyl carbonate. The aromatic alcohol is shown as phenol. The examples show that under comparable reaction conditions the transesterification of dimethyl carbonate results in a higher phenol conversion than the transesterification of diethyl carbonate. For instance, in Examples 2 and 8 similar reaction conditions in the same apparatus were applied in the transesterification of dimethyl carbonate and diethyl carbonate, respectively. Under the conditions shown the phenol conversion was significantly higher in the case of dimethyl carbonate than in the case of diethyl carbonate.

The Examples of U.S. Pat. No. 4,554,110 also disclose a transesterification of dialkyl carbonates with phenol as the aromatic alcohol where the dialkyl carbonates are dimethyl carbonate and diethyl carbonate. The Examples of U.S. Pat. No. 4,554,110 are further discussed below.

It is an object of the invention to provide the skilled person with tools to arrive at a higher conversion of the aromatic alcohol when a di($C_2$-$C_4$)alkyl carbonate is used as compared to when dimethyl carbonate is used.

It has now surprisingly been found that the conversion of di($C_2$-$C_4$)alkyl carbonates can be increased more than the conversion of dimethyl carbonate if the catalyst concentration and/or the residence time are chosen such that the product of said catalyst concentration and said residence time (said product being denoted as $P_a$) is at least 1.5 times the product of catalyst concentration and residence time for the transesterification of the aromatic alcohol with dimethyl carbonate to methyl aryl carbonate and methanol (said latter product being denoted as $P_m$) at a certain pre-set approach to the equilibrium (or percent of equilibrium) for the latter transesterification reaction. Additional advantages of the present invention are discussed below, including the Examples.

SUMMARY OF THE INVENTION

The present invention provides a process for the preparation of a diaryl carbonate by transesterification of an aromatic alcohol with a dialkyl carbonate in the presence of a transesterification catalyst during a period of time [$t_a$], in which the aryl moiety is selected from unsubstituted phenyl and mono-, di- and trisubstituted phenyl groups, in which the alkyl moiety is selected from $C_2$ to $C_4$ linear and branched alkyl groups, in which the catalyst concentration is designated [$c_a$], expressed as gram catalyst per gram of aromatic alcohol and dialkyl carbonate, in which the period of time [$t_m$] and catalyst concentration [$c_m$] are determined to arrive at a pre-set approach to the equilibrium for the transesterification of the aromatic alcohol with dimethyl carbonate to methyl aryl carbonate and methanol, in which the product [$c_a$]*$t_a$ is at least 1.5*[$c_m$]*$t_m$, under otherwise the same reaction conditions.

It was found that the product [$c_m$]*$t_m$ (herein referred to as $P_m$) influences the conversion of dimethyl carbonate, as demonstrated in the Examples below. If $P_m$ is multiplied by a certain factor (>1) the conversion increases. Also the conversion of di($C_2$-$C_4$)alkyl carbonates is influenced by the product [$c_a$]*$t_a$ (herein referred to as $P_a$), as also demonstrated in the Examples below. It was found that when $P_a$ and $P_m$ had the same value and $P_a$ was multiplied by the same factor (>1), the increase in the conversion of the di($C_2$-$C_4$)alkyl carbonate is proportionally greater, more specifically at relatively high P values.

The invention provides the skilled person with tools to arrive at a higher conversion of the aromatic alcohol when a di($C_2$-$C_4$)alkyl carbonate is used. This is surprising since the prior art (e.g. above-mentioned U.S. Pat. No. 5,344,954) suggests that the conversion of aromatic alcohol is significantly lower when such dialkyl carbonate is used instead of dimethyl carbonate.

In accordance with the invention, $P_a$ is at least 1.5*$P_m$. Further, according to the invention, said $P_m$ is determined to arrive at a pre-set approach to the equilibrium for the transesterification of the aromatic alcohol with dimethyl carbonate to methyl aryl carbonate and methanol.

The reaction between an aromatic alcohol and a dialkyl carbonate takes place in two steps. The first step is the transesterification of the aromatic alcohol with dialkyl carbonate to alkyl aryl carbonate and alkanol. This reaction is followed by the disproportionation of the alkyl aryl carbonate to diaryl carbonate and alkanol. The first reaction (transesterification) has the most unfavorable equilibrium.

With said term "pre-set approach to the equilibrium" it is meant the percent of equilibrium for the transesterification reaction in question, that is to say the extent (in %) to which equilibrium should be reached for said reaction. In other words, said pre-set approach to the equilibrium meets the following formula: percent of equilibrium (%)=$(K/K_{eq})*100$.

For the above specific reaction, wherein dimethyl carbonate is used, said K has the following definition: K=([methyl aryl carbonate]*[methanol])/([dimethyl carbonate]*[aromatic alcohol]).

Said K and the conversion of reactants are related. The higher the value of K, the more products are formed and consequently the higher the conversion. $K_{eq}$ is the equilibrium constant that is K at equilibrium. From the equilibrium constant the maximum conversion of reactants can be determined.

It is known that the reaction of aromatic alcohol, e.g. phenol, with dimethyl carbonate is an equilibrium reaction. The equilibrium constant has been determined and disclosed in various publications. For example, U.S. Pat. No. 5,426,207 discloses production of diaryl carbonate exemplified by the production of diphenyl carbonate by the reaction of phenol with dimethyl carbonate. For the transesterification reaction of phenol with dimethyl carbonate to methyl phenyl carbonate and methanol this specification discloses as a typical value of the equilibrium constant a result of $2.6*10^{-3}$. For the disproportionation reaction a typical value of $2.35*10^{-1}$ is disclosed. The journal article in Ind. Eng. Chem. Res., 2004, 43, 1897-1914 by W B Kim et al., discloses that the equilibrium constant for this transesterification reaction is $3*10^{-4}$ at 453K. It will be appreciated that the equilibrium constant may be dependent on the reaction conditions, including temperature and non-ideal concentrations.

Thus, in accordance with the present invention, $P_a$ for the conversion of the di($C_2$-$C_4$)alkyl carbonate is determined by a pre-set approach to the equilibrium (or pre-set conversion) for the transesterification of the aromatic alcohol with dimethyl carbonate to methyl aryl carbonate and methanol.

For the present invention it has been found that good results are obtained when the pre-set approach to the equilibrium for the transesterification of the aromatic alcohol with dimethyl carbonate to methyl aryl carbonate and methanol ranges from 70 to 100%, that is to say when $(K/K_{eq})*100$ for said reaction ranges from 70 to 100%. Preferably, said range is from 70 to less than 100%, more preferably from 80 to less than 100%, and most preferably from 90 to less than 100%. This will now be exemplified.

In the Examples below, it has been determined for the reaction of dimethyl carbonate with phenol that 90% of equilibrium is reached at a $P_m$ of 1.05. Therefore, in a case where the approach to the equilibrium for the transesterification of phenol with dimethyl carbonate to methyl phenyl carbonate and methanol is pre-set at 90%, then according to the invention $P_a$ for the reaction of di($C_2$-$C_4$)alkyl carbonate with phenol is at least 1.58 (=1.5*1.05).

It has further been found that the conversion of aromatic alcohol can be optimised when the reaction, wherein di($C_2$-$C_4$)alkyl carbonate is the dialkyl carbonate, gets closer to its equilibrium. Preferably, the factor by which $P_m$ is multiplied is chosen such that said reaction is run at least 50% of equilibrium, more preferably at least 55% of equilibrium, more preferably at least 60% of equilibrium, more preferably at least 70% of equilibrium, more preferably at least 80% of equilibrium, more preferably at least 90% of equilibrium, and most preferably at least 95% of equilibrium. This will now by exemplified by means of the reaction of diethyl carbonate with phenol.

In the Examples below, it has been determined for the reaction of diethyl carbonate with phenol that 50% of equilibrium is reached at a $P_a$ of about 1.9. Further, it has been determined, as already mentioned above, that for the reaction of dimethyl carbonate with phenol 90% of equilibrium is reached at a $P_m$ of 1.05. Therefore, in a case where the approach to the equilibrium for the transesterification of phenol with dimethyl carbonate to methyl phenyl carbonate and methanol is pre-set at 90%, the factor by which $P_m$ is to be multiplied is about 1.8 (=1.9/1.05) in order to arrive at 50% of equilibrium for the transesterification of phenol with diethyl carbonate to ethyl phenyl carbonate and methanol.

Good results have been achieved when the factor by which $P_m$ is multiplied varied between 1.5 and 500 so that the product $[c_a]*t_a$ is 1.5 to 500 times $[c_m]*t_m$, under otherwise the same reaction conditions. Preferably, the factor was selected from the range from 2 to 75.

The product $P_a$ can be selected within wide ranges. The skilled person will be able to select a suitable catalyst concentration and a suitable residence time to arrive at a feasible and practical conversion of the reactants. Suitable values for $P_a$ (=$[c_a]*t_a$) include values from 0.1 to 100, preferably from 0.5 to 50, $c_a$ being expressed in g/g and $t_a$ in seconds. For example, $P_a$ may be greater than 1.7, or may be at least 1.8 or at least 1.9 or at least 2.0 or at least 3.0 or at least 4.0, especially where the di($C_2$-$C_4$)alkyl carbonate is diethyl carbonate. Further, $P_a$ may be greater than 8.5, or may be at least 8.6 or at least 8.7 or at least 8.8 or at least 9.0 or at least 10.0, especially where the di($C_2$-$C_4$)alkyl carbonate is diisopropyl carbonate.

The aromatic alcohol is selected from unsubstituted phenol or mono-, di- or tri-substituted phenol. The substituents on the phenyl moiety can be selected from a wide range of organic groups. Suitable substituents include $C_1$-$C_4$ alkyl groups, $C_1$-$C_4$ alkoxy groups, and halides. Examples are methyl, ethyl, methoxy and ethoxy groups. The substituents can be present on any position in the ring. Hence, suitable substituted phenol compounds include o-, m- or p-cresol, o-, m- or p-ethyl phenol, o-, m- or p-chlorophenol, o-, m- or p-methoxy phenol, 2,3-, 2,4- and 3,4-dimethyl phenol. Preferably the aromatic alcohol is unsubstituted phenol.

The dialkyl carbonate that is used as starting material for the current process is a dialkyl carbonate in which the alkyl moieties have been selected from linear or branched $C_2$-$C_4$ alkyl moieties. Preferred are ethyl, propyl, isopropyl, and n-butyl moieties. Most preferably diethyl carbonate or diisopropyl carbonate is used as starting material. Preferably, when the dialkyl carbonate is diethyl carbonate the reaction is conducted such that the product $[c_a]*t_a$ is at least $3*[c_m]*t_m$. On the other hand, it has been found that when the reaction is conducted with diisopropyl carbonate, the product $[c_a]*t_a$ is preferably at least $20*[c_m]*t_m$.

As mentioned above, the Examples of U.S. Pat. No. 4,554,110 also disclose a transesterification of dialkyl carbonates with phenol as the aromatic alcohol, in which transesterification the dialkyl carbonates are dimethyl and diethyl carbonate. Examples 4, 5, 6, 9 and 10 of U.S. Pat. No. 4,554,110 is the only set of Examples wherein the sole variables were the following three: (1) type of carbonate, (2) amount of catalyst and (3) reaction time. See Table 1 below, below which table also some of the abbreviations used throughout the present specification are explained. Hereinafter, the term "Examples" in relation to U.S. Pat. No. 4,554,110 refers to Examples 4, 5, 6, 9 and 10 of U.S. Pat. No. 4,554,110 only.

TABLE 1

| Example in U.S. Pat. No. 4,554,110 | DAC | Catalyst amount (g) = A | Reaction time (h) = B | Yield of EPC or MPC (mole %) = C | Yield of DPC (mole %) = D | Yield of DPC, of theoretical (mole %) | Total yield (mole %) = C + D | $P_{DEC}$ = A * B | $P_{DMC}$ = A * B |
|---|---|---|---|---|---|---|---|---|---|
| 4  | DEC | 4 | 5  | 10.3 | 4.4  | 10.5 | 14.7 | 20 | — |
| 5  | DEC | 4 | 7  | 9.8  | 6.8  | 16.3 | 16.6 | 28 | — |
| 6  | DEC | 4 | 23 | 5.0  | 26.1 | 62.4 | 31.1 | 92 | — |
| 9  | DMC | 4 | 24 | 0    | 16.0 | 67.8 | 16.0 | — | 96 |
| 10 | DMC | 1 | 24 | 0    | 15.7 | 67.2 | 15.7 | — | 24 |

DAC = dialkyl carbonate; DEC = diethyl carbonate; DMC = dimethyl carbonate; EPC = ethyl phenyl carbonate; MPC = methyl phenyl carbonate; DPC = diphenyl carbonate; EtOH = ethanol; MeOH = methanol; PhOH = phenol.
The reaction time does not include the period (of 1 hour) for adding the DAC.

In the Examples of U.S. Pat. No. 4,554,110, 0.25 mole of DAC and 2 moles of phenol are used. In other words, there is a molar excess of 1.5 moles of phenol, as per 1 mole of DAC 2 moles of phenol are needed to convert DAC into DPC. As the phenol is in excess, the theoretical maximum yield of DPC is 0.25 mole, assuming that no DAC is removed. However, for those Examples where the DAC was DMC (Ex. 9-10), said assumption is not correct, as further discussed below (removal of DMC via an azeotrope with MeOH). The reaction sequence is as follows:

Transesterification: 2 PhOH+2 DAC→2 [EPC or MPC]+2 alcohol

Disproportionation: 2 [EPC or MPC]→DPC+DAC

Net reaction: 2 PhOH+DAC→DPC+2 alcohol

Table 1 in U.S. Pat. No. 4,554,110 mentions the yield of the intermediate EPC or MPC and the yield of the DPC (see also Table 1 above). Both said yields have been determined from a mixture which no longer contained the alcohol (EtOH or MeOH) as this was continuously removed from the reaction mixture by distillation (during the reaction), and which neither contained the remaining phenol as the reaction mixture was stripped under water aspirator vacuum (after the reaction). The total yield of the intermediate EPC or MPC and the DPC is also mentioned in Table 1 above. None of the Examples had a total yield of 100%. This means that the mixture from which the yields were determined also comprised other components, such as the catalyst (which had not been removed) and unidentified side-products. On the basis of the data given in U.S. Pat. No. 4,554,110 for the Examples, it is not possible to compare the conversion of DEC with the conversion of DMC as these conversions cannot be determined from the data given.

Further, Table 1 in U.S. Pat. No. 4,554,110 mentions the yield of the DPC based on the theoretical maximum yield (see also Table 1 above). In view of the limited data given in U.S. Pat. No. 4,554,110, it is not possible to verify whether the latter yield has been calculated correctly. However, it can be ascertained that there is an inconsistency between the "Yield of DPC" and the "Yield of DPC, of theoretical". If it is assumed that for all of the Examples (either DMC or DEC), the theoretical maximum yield of DPC is the same, namely 0.25 mole (see also above), then the "Yield of DPC, of theoretical" for Example 6 should have been higher than those for Examples 9 and 10, as the "Yield of DPC" for Example 6 was higher. Therefore, said "Yield of DPC, of theoretical" cannot be used for comparison purposes.

In the last two columns of Table 1 above, the product ($P_{DEC}$ for Ex. 4-6 and $P_{DMC}$ for Ex. 9-10) of catalyst amount and reaction time is mentioned. It is not correct to compare the products $P_{DEC}$ and $P_{DMC}$ for Examples 6 and 10, inter alia for the following reasons:

(1) The yields are not identical.

(2) "Yield of DPC, of theoretical" cannot be relied upon because of the above-mentioned inconsistency.

(3) The yield of a product is different from the conversion of a starting material used to make that product.

Indeed, $P_{DEC}$ for Example 6 is 3.8 (=92/24) times higher than $P_{DMC}$ for Example 10. However, inter alia for the above-mentioned reasons, this does not take away novelty of the present invention according to which $P_a$ is at least $1.5*P_m$.

Further, if instead of the "Yield of DPC, of theoretical" the "Total yield" (8th column of Table 1 above) is used, other comparison results are obtained. Said "Total yield" not only comprises DPC (final product) but also EPC or MPC (intermediate). Therefore, said "Total yield" is more in line with, but still not the same as, conversion of DAC. The "Total yield" of Example 5 (16.6 mole %) is closest to the "Total yield" of Examples 9 and 10 (where the yields differ by only 0.3%, i.e. 16.0 and 15.7 mole %, respectively). $P_{DEC}$ for Example 5 is almost the same as $P_{DMC}$ for Example 10, whereas it is 3.4 (=96/28) times lower than $P_{DMC}$ for Example 9. For this reason alone, said Examples can neither be destroying for novelty of the present invention according to which $P_a$ is at least $1.5*P_m$.

There is another reason why the Examples of U.S. Pat. No. 4,554,110 cannot be used for comparison with the invention of the present application. In said Examples, there is no question of a closed system. Namely, during the reaction the liberated alcohol was continuously removed by distillation (at a temperature of 180° C.). It is clear to a skilled person that the MeOH in Examples 9-10 forms an azeotrope with DMC (said azeotrope having a boiling point of 63° C.), whereas the EtOH in Examples 4-6 does not form an azeotrope with DEC. Therefore, in Examples 4-6, the DAC remains within the reaction system whereas in Examples 9-10 at least part of the DAC is removed. Further, as it is not disclosed in U.S. Pat. No. 4,554,110 that the DMC removed in Examples 9-10 was separated from the MeOH and then recycled back to the reaction, it seems that in Examples 9-10 less DAC was available for conversion than in Examples 4-6. However, there is no way to determine on the basis of the information given in U.S. Pat. No. 4,554,110, how much DMC was removed and how much remained available inside the reaction system. The foregoing renders comparison of Examples 4-6 with Examples 9-10 useless. In addition, the removal of DAC might have been responsible for the lack of MPC at the end of the reaction in Examples 9-10, as removal of one of the products of the second (disproportionation) reaction, namely DMC, would result in a higher conversion per time unit (i.e. more DPC, less DMC).

In conclusion, a skilled person cannot derive from U.S. Pat. No. 4,554,110 the technical measure of the present invention, implying that the product $[c_a]*t_a$ is at least $1.5*[c_m]*t_m$. Therefore, said measure is not disclosed in U.S. Pat. No. 4,554,110, not explicitly and neither implicitly.

The selection of the transesterification catalysts that are to be used in the present process is not critical. Any transesterification catalyst can be used. Many catalysts are known. U.S. Pat. No. 5,344,954 describes a long list, including those catalysts that are known from a variety of prior art documents. Suitable catalysts include oxides, hydroxides, alcoholates, amides and hydrides of alkali and alkaline earth metals. Salts of alkali metals or alkaline earth metals include alkali metal carboxylates, carbonates and bicarbonates. The metal is preferably selected from sodium, potassium, magnesium and calcium, sodium and potassium being specifically preferred. Preferred catalysts are alkali metal hydroxides, such as sodium or potassium hydroxide, and alcoholates, such as sodium or potassium methanolate or ethanolate.

Further catalysts can be Lewis acid metal compounds, such as $AlX_3$, $TiX_3$, $TiX_4$, $VX_5$, $ZnX_2$, $FeX_3$ and $SnX_4$, X being selected from the group consisting of hydrogen, acetoxy, alkoxy or arylalkoxy groups. The most preferred catalyst of this group is tetra alkoxy titanium with the alkoxy group containing from 1 to 6 carbon atoms. Examples are titanium tetramethoxide, titanium dimethoxide, titanium diethoxide, titanium tetrapropoxide, and titanium tetrabutoxide. The alkoxide group can be linear or branched and linear alkoxide groups are preferred.

Another type of catalysts includes lead compounds comprising carbonate, carboxylate, hydroxide and phosphine groups. Examples are lead acetate and lead carbonate.

Combinations of the above types of catalysts are also possible, as shown in U.S. Pat. No. 5,344,954. Further catalysts are disclosed in U.S. Pat. No. 5,747,609.

Heterogeneous catalysts are also feasible. Suitable catalysts include those disclosed in U.S. Pat. No. 5,344,954, viz. mixed oxides of silicon and titanium and titanium dioxides.

Minor amounts of catalyst may be used. In general the concentrations of catalysts ($c_a$) may vary from 0.001 to 2% wt, based on the total weight of the reactants, i.e. dialkyl carbonate and aromatic alcohol. Preferred concentrations include 0.005 to 1% wt, more preferred concentrations being from 0.01 to 0.5% wt.

Although the conversion of dialkyl carbonate to diaryl carbonate requires two molecules of aromatic alcohol per molecule dialkyl carbonate it is not necessarily advantageous to employ stoichiometric amounts of aromatic alcohol and dialkyl carbonate. Since the reaction is subject to equilibrium not all reactants will react to completion. Hence, in practice recycle of unconverted reactants is desirable. A surprising advantage of the present invention is that the number of recycles can be reduced considerably, as is demonstrated in the Examples below.

If an excess of aromatic alcohol is being used, unconverted aromatic alcohol is to be recycled. In case of a substoichiometric amount of aromatic alcohol, a significant fraction of dialkyl carbonate is suitably recycled. Therefore, the molar ratio of aromatic alcohol to dialkyl carbonate ranges preferably from 0.2:1 to 10:1. Since the recycle of dialkyl carbonate is conducted more easily than the recycle of aromatic alcohol, the molar ratio of aromatic alcohol to dialkyl carbonate ranges preferably from 0.2:1 to 2:1. When an excess of aromatic alcohol is used, the molar ratio of aromatic alcohol to dialkyl carbonate ranges preferably from 2.5:1 to 10:1.

Suitable reaction conditions have been described in U.S. Pat. No. 5,344,954 and U.S. Pat. No. 5,747,609. The reaction temperature may be varied depending on the dialkyl carbonate used and diaryl carbonate produced. In general, the reaction temperature may range from 50 to 350° C., preferably from 120 to 280° C. The reaction pressure is not critical either and can be selected within wide ranges. It is feasible to conduct the reaction at sub-atmospheric, atmospheric and super-atmospheric pressure. The reaction pressure is generally from 0.01 to 100 bar (1 kPa to 10 MPa), preferably from 1 to 50 bar.

The reaction time ranges suitably from 2 minutes (120 s) to 50 hours ($180*10^3$ s), preferably from 5 minutes to 25 hours (0.3 to $90*10^3$ s), more preferably from 10 minutes to 12.5 hours (0.6 to $45*10^3$ s).

The process of the present invention can suitably be carried out in a batch mode. This will enable the skilled artisan to determine the desired concentration of catalyst and the desired reaction time. The drawback of a batch-wise reaction is evidently the necessity to fill and empty the reaction vessel used. It is therefore advantageous to conduct the present process as a continuous process. In such a mode the desired quantities of aromatic alcohol and dialkyl carbonate are continuously fed into a first reaction zone. Preferably, the process according to the invention is conducted in two steps, the first step being an esterification process and the second step being a disproportionation process. As has been described in U.S. Pat. No. 5,344,954 in the esterification step the aromatic alcohol reacts with the dialkyl carbonate to alkyl aryl carbonate and alkyl alcohol. The alkyl alcohol is removed from the resulting reaction mixture. Suitably, the process is conducted in a reactive distillation mode. The way to carry out such a mode has also been disclosed in U.S. Pat. No. 5,344,954.

When the catalyst used in such continuous process is homogeneous the catalyst concentration $c_a$ is calculated as the amount of catalyst per time unit passed into the first reaction zone per the combined amounts of dialkyl carbonate and aromatic alcohol fed into the first reaction zone in the same time unit. The period of time ($t_a$) in which the dialkyl carbonate is reacted in the presence of a transesterification catalyst is proportional to the weight hourly space velocity. The catalyst is commonly passed on with the remainder of the reaction mixture, including unreacted dialkyl carbonate, alkyl aryl carbonate, and aromatic alcohol to a second reaction zone in which the disproportionation of alkyl aryl carbonate to diaryl carbonate and dialkyl carbonate takes place. In the second reaction zone also the further transesterification of alkyl aryl carbonate with the aromatic alcohol to the diaryl carbonate may take place. The resulting reaction mixture thereof generally includes dialkyl carbonate, diaryl carbonate, aromatic alcohol and alkyl alcohol. This mixture is usually separated into a top fraction containing the dialkyl carbonate and alkyl alcohol. The bottom fraction generally comprises the aromatic alcohol and the diaryl carbonate. The two fractions may be subsequently subjected to further separation steps, such as distillation, to separate the alkyl alcohol from the dialkyl carbonate and the aromatic alcohol from the diaryl carbonate, respectively. Any catalyst that is discharged from the second reaction zone is suitably separated from the bottom fraction.

When the process is conducted in the presence of a heterogeneous catalyst, the catalyst is generally immobilised in the first reaction zone. The catalyst, therefore, is not entrained with the product and passed to the second reaction zone. Instead the catalyst remains in the first reaction zone. Variations in $c_a$ can be easily accomplished by varying the amount of catalyst. Another way of influencing P is to vary the weight hourly space velocity of the reactants. A second catalyst may be present in the second reaction zone.

In the disproportionation zone, any of the above-mentioned transesterification catalysts may be present. For convenience sake the same homogeneous catalyst is suitably used. In case of a heterogeneous catalyst the use of the same or another heterogeneous catalyst can be contemplated. On the other hand, also the use of one of the homogeneous catalysts is feasible.

The diaryl carbonate produced in the process of the present invention is suitably used in the preparation of polycarbonates by the polymerisation with a dihydroxy aromatic compound, preferably with Bisphenol A.

The invention is further illustrated by means of the following experiments.

EXAMPLES

In order to show the advantages of the present invention a number of batch experiments were conducted using phenol as aromatic alcohol, as summarized in Table 2. In Exp. nos. 1-2, the dialkyl carbonate was dimethyl carbonate (DMC), which is not in accordance with the invention. In Exp. nos. 3-8 and 9-16, respectively, the dialkyl carbonate was diethyl carbonate (DEC) and diisopropyl carbonates (DiPC), respectively, which is in accordance with the invention.

In a stainless steel reactor (autoclave) phenol, dialkyl carbonate and tetra(n-butyl) titanium (transesterification catalyst) were mixed at a constant temperature of 180° C. The molar ratio of dialkyl carbonate to phenol was 1:3. The amount of catalyst (in mg/g reactants) and the residence time (in s) are shown in Table 2. The product of said catalyst amount and residence time (in g.s/g reactants) is also shown in Table 2.

In the experiments of these Examples, a closed reaction system was used. There was question of a (batch) reaction wherein all of the starting materials and (intermediate) products remained in the reaction system. In said experiments, a 250 ml batch autoclave was used. No reflux with cooling was used. During the experiments, the autoclave was about half full of liquid. Before heating up to the reaction temperature of 180° C., the gas cap was flushed with nitrogen (about 1 bara). Phenol and the catalyst were then added. The autoclave, containing phenol and catalyst, was sealed and heated up to the reaction temperature. The dialkyl carbonate (DAC) was put in another vessel and also heated to the reaction temperature. At t=0, injection of the DAC into the autoclave under its own vapor pressure was started. Small (1 ml) samples of the reaction liquid were removed periodically and analyzed. That is to say, the amounts of alkyl phenyl carbonate, alkanol, phenol (PhOH) and dialkyl carbonate were determined. Based on said amounts, the quotient K was determined, said K being ([alkyl phenyl carbonate]*[alkanol])/([dialkyl carbonate]*[PhOH]).

The values for K as experimentally determined are shown in Table 2, which also shows the percent of equilibrium which was achieved in each case and which is related to K as follows:

percent of equilibrium (%)=$(K/K_{eq})$*100.

TABLE 2

| Exp. No. | Dialkyl carbonate | Catalyst (mg/g) | Residence time (s) | P (g·s/g) | Percent of equilibrium (%) | K (*$10^{-3}$) |
|---|---|---|---|---|---|---|
| 1 | DMC | 0.6 | 1750 | 1.05 | 90 | 1.86 |
| 2 | DMC | 0.6 | 3500 | 2.10 | 99 | 2.05 |
| 3 | DEC | 1.1 | 955 | 1.05 | 26 | 1.1 |
| 4 | DEC | 1.1 | 1910 | 2.10 | 53 | 2.3 |
| 5 | DEC | 1.1 | 3910 | 4.30 | 90 | 3.9 |
| 6 | DEC | 0.67 | 1570 | 1.05 | 22 | 1.0 |
| 7 | DEC | 0.67 | 3140 | 2.10 | 47 | 2.0 |
| 8 | DEC | 0.67 | 7200 | 4.82 | 90 | 3.9 |
| 9 | DiPC | 1.76 | 600 | 1.06 | 1 | 0.05 |
| 10 | DiPC | 1.76 | 1200 | 2.11 | 2 | 0.12 |
| 11 | DiPC | 1.76 | 2400 | 4.22 | 6 | 0.34 |
| 12 | DiPC | 1.76 | 18500 | 32.56 | 90 | 5.5 |
| 13 | DiPC | 2.48 | 420 | 1.04 | 1 | 0.05 |
| 14 | DiPC | 2.48 | 840 | 2.08 | 2 | 0.14 |
| 15 | DiPC | 2.48 | 1680 | 4.17 | 6 | 0.37 |
| 16 | DiPC | 2.48 | 14000 | 34.72 | 90 | 5.5 |

Comparisons between the experiments with the same P for a given dialkyl carbonate show that the conversions or K's (and percents of equilibrium which are related thereto) are very similar, within the experimental errors. Compare for example Exp. no. 3 with Exp. no. 6.

In the present Examples, $K_{eq}$ for the transesterification reaction of DEC and phenol was experimentally determined to be $4.3*10^{-3}$, about 2 times higher than the $K_{eq}$ for the transesterification reaction of DMC and phenol as determined under the same circumstances. This is shown in Table 3 and in FIG. 1. $K_{eq}$ for the reaction of DiPC and phenol is also shown in Table 3.

FIG. 1 comprises a graph wherein P (in g.s/g), being the product of catalyst concentration and residence time, is plotted against K as experimentally determined, for the reactions of DMC and DEC with phenol. The two plots in said graph were made assuming first order approach to equilibrium. The $K_{eq}$ values of $2.1*10^{-3}$ and $4.3*10^{-3}$ for the transesterification reactions of phenol with DMC and DEC, respectively, are shown as horizontal lines in said graph. The relationship between K and P, as determined in the foregoing way, is also shown in Table 3. Table 3 mentions the same relationship (determined in the same way) for the reaction of DiPC and phenol.

TABLE 3

| Dialkyl carbonate (DAC) | "e" = about 2.72 |
|---|---|
| DMC | $K_{eq} = 2.1 * 10^{-3}$<br>$K = K_{eq}(1 - e^{(0.25-2.1P)})$<br>$P = (0.25 + \ln[K_{eq}] - \ln[K_{eq} - K])/2.1$ |
| DEC | $K_{eq} = 4.3 * 10^{-3}$<br>$K = K_{eq}(1 - e^{(0.25-0.5P)})$<br>$P = (0.25 + \ln[K_{eq}] - \ln[K_{eq} - K])/0.5$ |
| DiPC | $K_{eq} = 5.9 * 10^{-3}$<br>$K = K_{eq}(1 - e^{(0.25-0.08P)})$<br>$P = (0.25 + \ln[K_{eq}] - \ln[K_{eq} - K])/0.08$ |

The experiments show that whereas the doubling of P in case of DMC only caused an increase in conversion, as evidenced by K, of about 10%, the doubling of the same P in case of DEC or DiPC resulted in 100% or more increase of the level to equilibrium. This is also depicted in FIG. 1 for the reactions of DMC and DEC with phenol. That is to say, when $P_a$ (for DEC) and $P_m$ (for DMC) have the same value and $P_a$ and $P_m$ are then multiplied by the same factor (>1), the increase in the conversion (i.e. K) of DEC is proportionally greater, more specifically at relatively high P values.

Further, the experiments show that, as evidenced by a higher value of K, more specifically at relatively high P values, a higher overall conversion is attainable in case of DEC and DiPC than in case of DMC. This advantageous effect of the present invention is clearly visualized in FIG. 1. Referring to the graph in said FIG. 1, at for example 90% of the equilibrium, that is to say at K=1.9*10$^{-3}$ (for DMC reaction) and K=3.9*10$^{-3}$ (for DEC reaction), $P_a$ for the DEC reaction (about 5.2) is indeed greater than P for the DMC reaction (about 1.2). Generally, a higher P is considered to be disadvantageous, because more catalyst and/or longer residence time are needed. On the other hand, however, the present inventors found that at this higher P for the DEC reaction, the conversion (i.e. K) is substantially greater than could be obtained in the DMC reaction at the same or a lower P value.

The present experiments were carried out as a batch reaction wherein the reaction mixture was not recycled over the reactor. In other words, there was only "one pass". Using DEC thus translates into a higher conversion "per pass" than using DMC. This indicates that, because more is converted in one pass, less reaction mixture has to be recycled during continuous production. Less recycling of the reaction mixture translates into higher production of desired product per time unit and/or smaller production unit at the same level of production of desired product per time unit. In such case, the process can be greatly simplified and costs can be considerably lowered.

The invention claimed is:

1. A process for the preparation of a diaryl carbonate by transesterification of an aromatic alcohol with a dialkyl carbonate in the presence of a transesterification catalyst during a period of time [$t_a$], in which the aryl moiety is selected from unsubstituted phenyl and mono-, di- and trisubstituted phenyl groups,
in which the alkyl moiety is selected from $C_2$ to $C_4$ linear and branched alkyl groups,
in which the catalyst concentration is designated [$c_a$], expressed as gram catalyst per gram of aromatic alcohol and dialkyl carbonate,
in which the period of time [$t_m$] and catalyst concentration [$c_m$] are determined to arrive at a pre-set approach to the equilibrium for the transesterification of the aromatic alcohol with dimethyl carbonate to methyl aryl carbonate and methanol,
in which the product [$c_a$]*$t_a$ is at least 1.5*[$c_m$]*$t_m$, under otherwise the same reaction conditions.

2. A process as claimed in claim 1, in which the pre-set approach to the equilibrium for the transesterification of the aromatic alcohol with dimethyl carbonate to methyl aryl carbonate and methanol ranges from 70 to 100%.

3. A process as claimed in claim 1, in which [$c_a$]*$t_a$ is the product of [$c_m$]*$t_m$ with such a factor that the reaction is run at least 50 percent of equilibrium.

4. A process as claimed in claim 1, in which the catalyst concentration $c_a$ ranges from 0.001 to 2% wt, based on the total weight of the reactants.

5. A process as claimed in claim 1, in which the period of time $t_a$ ranges from 2 minutes (120 s) to 50 hours (180*10$^3$ s).

6. A process as claimed in claim 1, in which the product [$c_a$]*$t_a$ ranges from 0.1 to 100, preferably from 0.5 to 50, $c_a$ being expressed in g/g and $t_a$ in seconds.

7. A process as claimed in claim 1, which is carried out as a continuous process.

8. A process as claimed in claim 1, which is conducted in a reactive distillation mode.

9. A process as claimed in claim 1, in which the aromatic alcohol is phenol.

10. A process as claimed in claim 1, in which the $C_2$ to $C_4$ alkyl moiety is selected from the group consisting of ethyl and isopropyl.

11. A process as claimed in claim 1, in which the reaction conditions include a pressure ranging from 0.01 to 100 bar and a reaction temperature ranging from 50 to 350° C.

12. A process as claimed in claim 1, in which the product [$c_a$]*$t_a$ is 1.5 to 500 times [$c_m$]*$t_m$, under otherwise the same reaction conditions.

13. A process as claimed in claim 12, in which the product [$c_a$]*$t_a$ is at least 3*[$c_m$]*$t_m$ when the dialkyl carbonate is diethyl carbonate.

14. A process as claimed in claim 12, in which the product [$c_a$]*$t_a$ is preferably at least 20*[$c_m$]*$t_m$ when the dialkyl carbonate is diisopropyl carbonate.

* * * * *